(12) United States Patent
Yamazaki

(10) Patent No.: US 8,922,762 B2
(45) Date of Patent: Dec. 30, 2014

(54) SPECTROSCOPIC MEASURING APPARATUS WITH MONITORING CAPABILITY

(75) Inventor: Toshio Yamazaki, Tokyo (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 0 days.

(21) Appl. No.: 13/879,459

(22) PCT Filed: Oct. 27, 2011

(86) PCT No.: PCT/JP2011/074783
§ 371 (c)(1),
(2), (4) Date: Apr. 15, 2013

(87) PCT Pub. No.: WO2012/057254
PCT Pub. Date: May 3, 2012

(65) Prior Publication Data
US 2013/0201475 A1    Aug. 8, 2013

(30) Foreign Application Priority Data

Oct. 29, 2010   (JP) .................................. 2010-243381

(51) Int. Cl.
*G01J 3/02*        (2006.01)
*G02B 27/10*       (2006.01)
*G01J 3/28*        (2006.01)
*G01J 3/04*        (2006.01)
*G01N 21/31*       (2006.01)
*G02B 27/14*       (2006.01)
*G01N 21/17*       (2006.01)

(52) U.S. Cl.
CPC ............ *G01J 3/0256* (2013.01); *G01J 3/0264* (2013.01); *G01J 3/021* (2013.01); *G01N 2021/1793* (2013.01); *G02B 27/1066* (2013.01); *G01J 3/2823* (2013.01); *G01J 3/04* (2013.01); *G01J 3/0208* (2013.01); *G01J 3/0237* (2013.01); *G01N 21/31* (2013.01); *G02B 27/143* (2013.01); *G01J 3/0243* (2013.01)
USPC .......................................................... 356/73

(58) Field of Classification Search
USPC ...................... 356/72–73, 302, 326, 328, 334
See application file for complete search history.

(56) References Cited

U.S. PATENT DOCUMENTS 4,088,410 A * 5/1978 Smith ........................... 356/390
4,844,617 A * 7/1989 Kelderman et al. ........... 356/624

(Continued)

FOREIGN PATENT DOCUMENTS

IT    EP 1178283   *  7/2000  ............. G01C 11/02
JP    2001-208979      8/2001

(Continued)

OTHER PUBLICATIONS

Notification of Transmittal of Translation of the International Preliminary Report on Patentability for PCT/JP2011/074783, mailed May 23, 2013.

(Continued)

*Primary Examiner* — Abdullahi Nur
(74) *Attorney, Agent, or Firm* — Greenblum & Bernstein, P.L.C.

(57) ABSTRACT

A spectroscopic measuring apparatus with monitoring capability includes a first optical path that extends from a measuring object through an optical system and a slit of a slit-mirror block to a spectroscope main body and a second optical path that extends from the measuring object through the optical system and a mirror face of the slit-mirror block to a two-dimensional photographing unit. The slit and spectroscope main body are integrated into a spectroscopic unit.

7 Claims, 4 Drawing Sheets

(56) References Cited

U.S. PATENT DOCUMENTS

| | | | |
|---|---|---|---|
| 5,995,645 A | | 11/1999 | Soenksen et al. |
| 7,518,710 B2 * | | 4/2009 | Gao et al. ............ 356/73 |
| 2009/0213362 A1 * | | 8/2009 | Nakamura et al. ......... 356/72 |

FOREIGN PATENT DOCUMENTS

| | | |
|---|---|---|
| JP | 2001-289619 | 10/2001 |
| JP | 2001-525580 | 12/2001 |
| JP | 2004-145372 | 5/2004 |
| JP | 2007-086470 | 4/2007 |
| JP | 2008-281513 | 11/2008 |
| JP | 2009-086573 | 4/2009 |
| WO | 99/28856 | 6/1999 |

OTHER PUBLICATIONS

Australia Office action in Australian Patent Application No. 2011321433, mail date is Apr. 15, 2014.

Zhang Yu et al., "Moving Target Imaging System Based on Joint Area CCD", Semiconductor Optoelectrics vol. 31, No. 4 (Aug. 2010).

China Office action, mail date is Jul. 3, 2014.

* cited by examiner

SPECTROSCOPIC MEASURING APPARATUS WITH MONITORING CAPABILITY

TECHNICAL FIELD

The present invention relates to a spectroscopic measuring system, and particularly, to a downsized spectroscopic measuring apparatus capable of monitoring the vicinities of a measuring field to be scanned.

BACKGROUND ART

There is known a system of scanning and spectroscopically measuring a measuring object, to early diagnose a skin disease such as a melanoma. A spectroscopic measuring apparatus has a spectroscope (first optical device) and an autofocus controller (second optical device) and arranges a slit mirror in the vicinity of a focus of an objective optical system. Reflected light from the slit mirror is detected with a position sensor, to autofocus-control the objective optical system. Transmitted light straight from the slit is made incident to the spectroscope and is spectroscopically measured with a diffraction grating. Scanning the measuring object provides two-dimensional spectroscopic information about the measuring object. With the use of part of the reflected light from the slit mirror, it is possible to monitor, with a two-dimensional camera, the measuring object other than the spectroscopically measured field. Related arts are, for example, Japanese Unexamined Patent Application Publications No. 2001-289619, No. 2001-208979, No. 2004-145372, and No. 2007-086470.

SUMMARY OF INVENTION

Problem to be Solved by Invention

The above-mentioned related art, however, is configured to connect the separate spectroscope to a main body including the slit mirror. Transmitted light from the slit is again collected with an optical system, and in this state, a measuring position must be identified. For this, the light must be passed through an incident slit to the spectroscope such as the grating. This raises problems of elongating the total length of the apparatus and needing a large-scale scanning device.

Means to Solve Problem

In considering the above-mentioned problems, the present invention downsizes a spectroscope, reduces the weight of a scanning device, and increases the scanning speed and operability of a measuring object. The present invention allows a spectroscopic object region to be monitored in real time with two-dimensional monitor images.

According to a technical aspect of the present invention, there is provided a spectroscopic measuring apparatus with monitoring capability. The apparatus includes a first optical path that guides a first beam from a measuring object to a spectroscope main body, a second optical path that guides a second beam from the measuring object to a two-dimensional photographing unit, an optical system that passes the first and second optical paths, and a reflection block that transmits the first beam passed through the optical system and reflects the second beam passed through the optical system, the reflection block having a reflection area to reflect beams other than the first beam and a slit area formed in the reflection area and positioned in the first optical path and in a focal plane of the optical system, the spectroscope main body being arranged adjacent to the reflection block.

MODE OF IMPLEMENTING INVENTION

Figure 1:
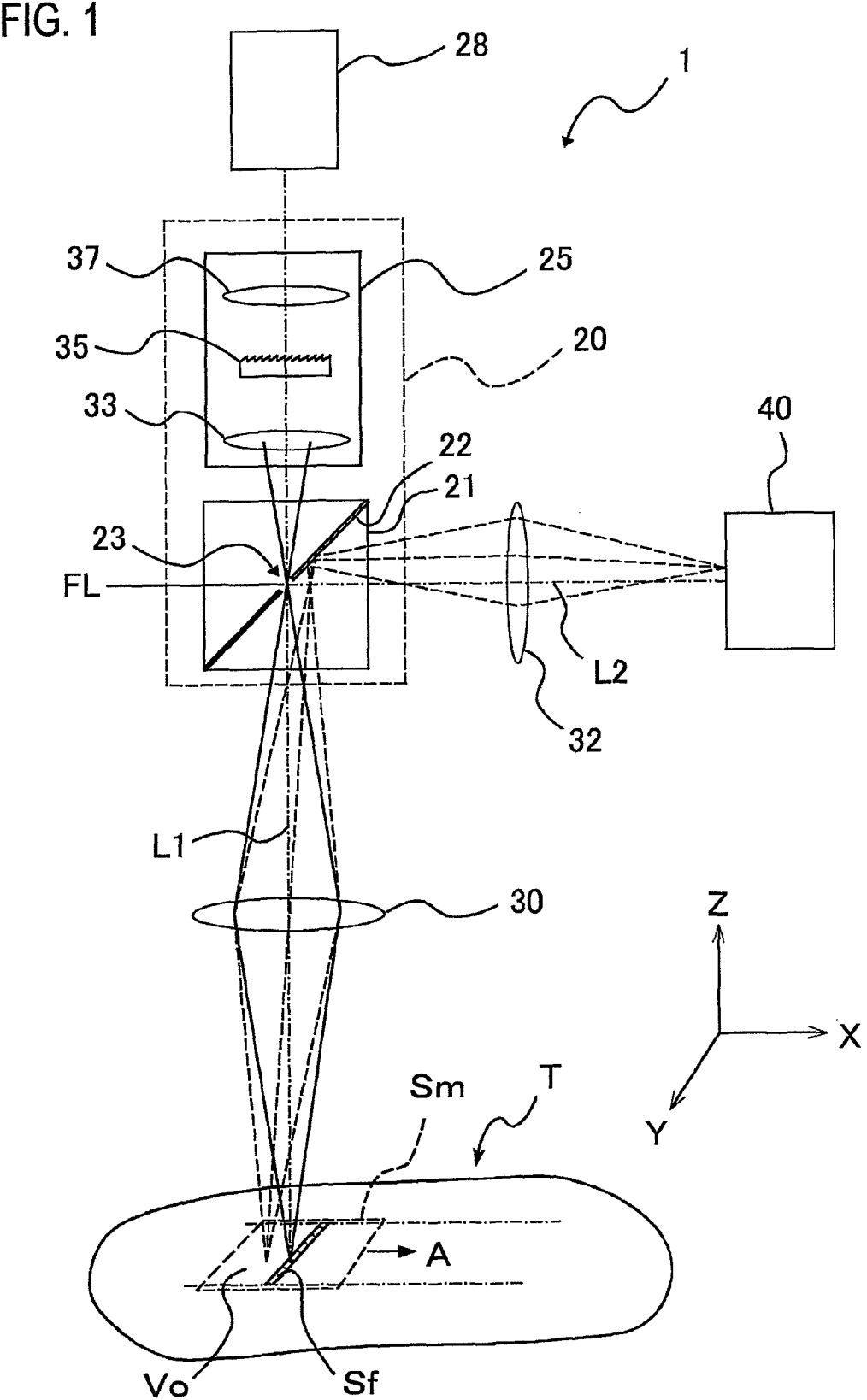
FIG. 1 is a schematic view of a spectroscopic measuring system according to the present invention.

An embodiment of the present invention will be explained with reference to FIGS. 1 to 4. According to the embodiment, a spectroscopic measuring system 1 is an apparatus for scanning and spectroscopically measuring a predetermined region on a skin surface. In the drawings, directions are expressed on an XYZ orthogonal coordinate system. The spectroscopic measuring system 1 according to the embodiment of the present invention includes an optical system 30, a reflection block 21 having a slit 23 that is at a focal line FL and serves as a light transmission area, a spectroscope main body 25 that spectroscopically measures a spectroscopic measuring field Sf that corresponds to the slit 23 and is linearly distributed, and a two-dimensional photographing unit 28 that provides a spectroscopic result.

The spectroscopic measuring apparatus 1 is installed in a scanning unit (not illustrated), to repeatedly scan and measure a measuring target T on a skin surface in a direction A that is parallel to an X-axis. The spectroscopic measuring field Sf is a linear area corresponding to an instantaneous field of view of a spectroscopic unit 20 and reflected light (including light emission and fluorescence) therefrom advances along an optical path L1 that is an optical axis of the optical system 30, converges on and transmits through the slit 23, and reaches the spectroscope main body 25. Reflected light from a peripheral region Vo of the spectroscopic measuring field Sf is reflected by a reflection plane part 22 of the reflection block 21, advances along an optical path L2, and forms an image on a photographing plane of a two-dimensional photographing unit 40.

In FIG. 1, a measuring field Sm of the two-dimensional image obtained by the two-dimensional photographing unit 40 and the spectroscopic measuring field Sf of the spectroscopic unit 20 move in the direction A according to time due to scanning.

The optical system 30 includes an objective optical system and is controlled and moved in the direction of the optical axis with an autofocus mechanism (not illustrated), so that the focal level FL is maintained at the position of the slit 23. The autofocus mechanism may be based on a related art. If the mechanism of the above-mentioned patent literature Japanese Unexamined Patent Application Publication No. 2007-086470 is employed, a laser beam scattered on the measuring target T and branched from the optical path L2 is detectable with a position sensor (not illustrated).

<Slit-Mirror Block>

Figure 2:
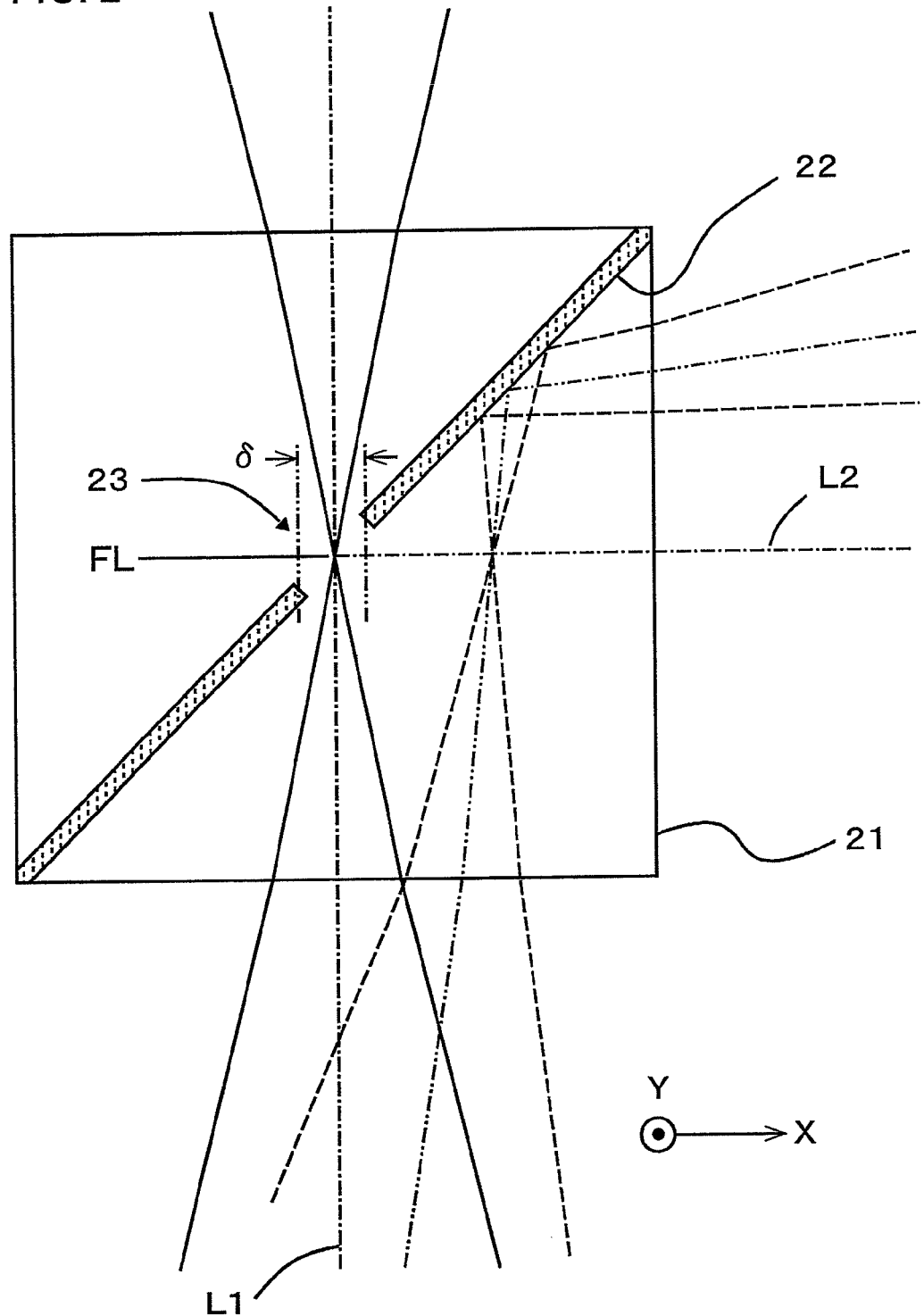
FIG. 2 is a schematic view of a partial transmission block according to the present invention.

The reflection block (hereinafter referred to as the slit-mirror block) 21 having the slit 23, i.e., the light transmission area serves as a slit of the spectroscopic unit 25 to be explained later and as a mirror to reflect observation light toward the two-dimensional photographing unit 40. FIG. 2 is a model view illustrating the slit-mirror block. The slit-mirror block 21 forms, in a prism having a predetermined refractive index, a reflection plane part obliquely crossing the optical axis L1. The reflection plane part 22 has a mirror face having an elongated opening. The block is typically a rectangular parallelepiped and may be constituted by bonding two triangle prisms together with the mirror face interposed between them.

The elongated opening is the slit 23 and is made of a material having the same refractive index as the prism, and therefore, transmitted light straightly advances through the slit 23. A main axis of the slit 23 is arranged in a Y-axis direction. One face of the triangle prism serving as a bonding face may be coated with a metal thin film to form a thin mirror-face film, thereby constituting the reflection part 22 and slit 23.

The focal level FL of the optical system 30 is always positioned at the slit 23, and therefore, reflected light only from the spectroscopic measuring field Sf, which is a specific elongated area in the measuring field Sm, passes the slit 23. Reflected light from the remaining region Vo is reflected by the reflection area 22, travels along the optical path L2, and fauns an image in the two-dimensional photographing unit 40. Another idea may be suggested to form a transmission area in a plate mirror and obliquely arrange the plate mirror to serve a partial transmission member. In this case, the transmission area is oblique, and therefore, ghost will occur due to multiple reflection in the plate mirror depending on the thickness of the plate mirror. This makes it difficult to correctly carry out spectroscopic measurement. The slit-mirror block 21 of the embodiment is integrated with the spectroscope main body to be explained later, to realize compactness and correct spectroscopic measurement. The sandwiching configuration of the mirror face according to the embodiment ensures mechanical stability and reliability.

According to the present embodiment, the mirror face 22 changes the optical path by 90 degrees. The angle of the mirror face 22 with respect to the optical axis L1 is not limited to 45 degrees but is optional.

<Spectroscopic Unit>

The spectroscopic unit 20 according to the present invention includes the slit-mirror block 21 that serves the slit and the spectroscope main body 25 that includes a grating 35 arranged adjacent to the slit-mirror block 21. The grating 35 may be of a transmission type or of a reflection type.

Depending on the position of the slit 23 of the slit-mirror block 21, the specific linear area (spectroscopic measuring field) Sf is selected on the measuring target T. Namely, the spectroscopic measuring field Sf is an instantaneous field of view and a real image thereof is formed by the optical system 30 at the focal level FL. An effective width δ of the slit 23 corresponds to an X-direction width of the spectroscopic measuring field Sf.

Reflected light from the spectroscopic measuring field Sf is transmitted through the slit 23 and is changed by a collimator lens 33 into a parallel pencil, which is spectrally separated by the grating 35 according to the position of the spectroscopic measuring field Sf in the Y-axis direction. The spectroscopic result is passed through a condensing optical system 37 and is obtained by the two-dimensional photographing unit 28 as a two-dimensional image containing positional information and spectral information.

Output data from the two-dimensional photographing unit 28 may be monitored as it is, or is stored in connection with a monitor image of the measuring field Sm to be explained later.

<Real-Time Monitoring>

The two-dimensional photographing unit 40 includes an area CCD camera having a two-dimensional image sensor, to obtain a two-dimensional image (hereinafter referred to as a monitor image) of the measuring field Sm that is a peripheral region of the spectroscopic measuring field Sf. When a skin surface is scanned and spectroscopically measured in the direction A (X-axis direction), it is possible to always obtain two-dimensional images of the region Vo of the measuring field Sm except the spectroscopic measuring field Sf. In FIGS. 1 and 2, a reflected beam from the region Vo out of the spectroscopic measuring field Sf is indicated with dotted lines.

The spectroscopic measuring field Sf moves according to time due to scanning. With the measuring field Sm being displayed, it is easy to confirm in real time the spectroscopic measuring field Sf that is presently measured. No reflected light from the spectroscopic measuring field Sf reaches the two-dimensional photographing unit 40, and therefore, a real image of the slit 23 in the monitor image is displayed in black. Accordingly, the position of the spectroscopic measuring field Sf is easily and correctly confirmable.

Figure 3:
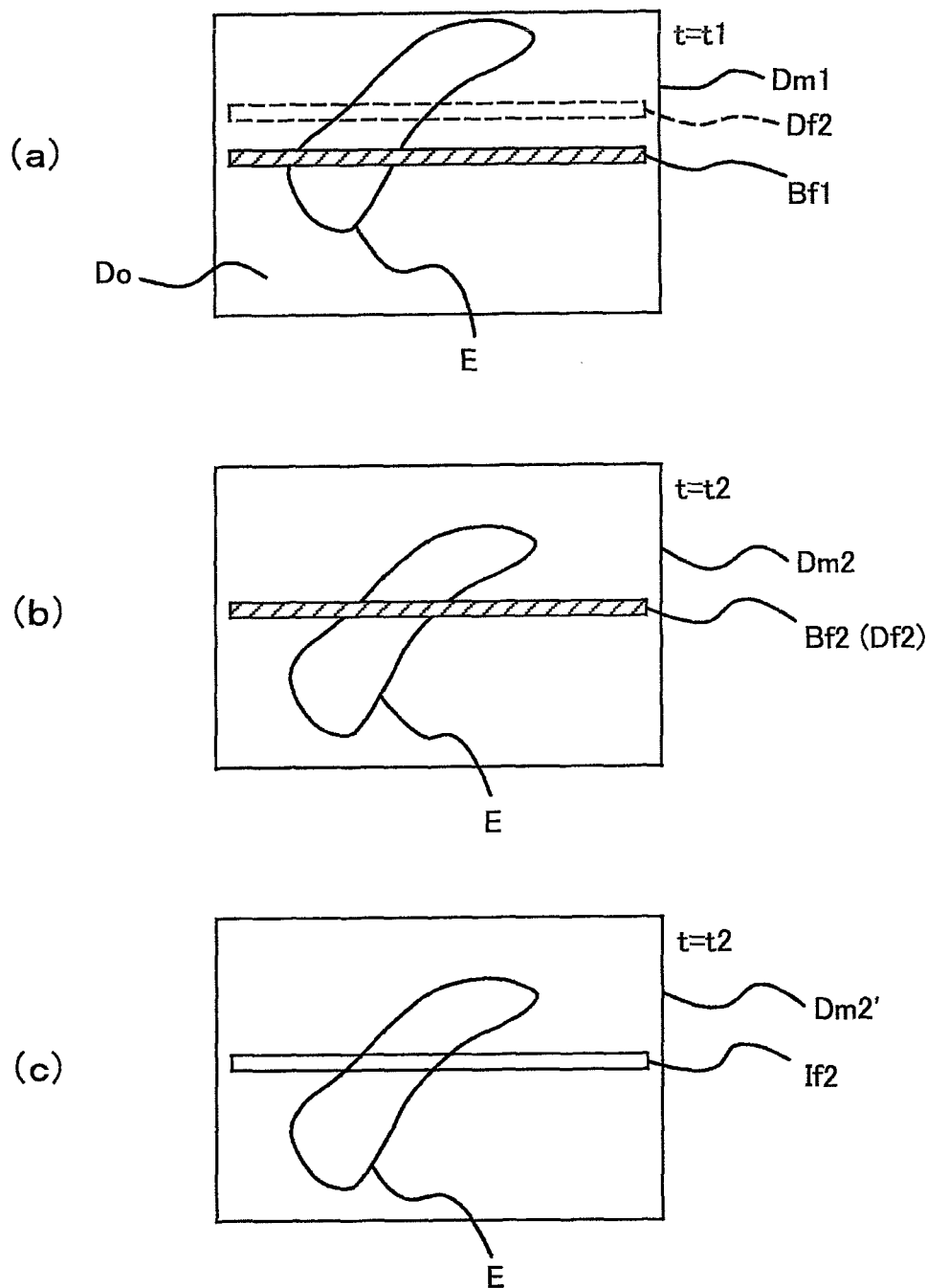
FIG. 3 is a schematic view of a monitor display of the spectroscopic measuring system according to the present invention.

FIG. 3 schematically illustrates an improved display of the monitor image by the two-dimensional photographing unit. As mentioned above, the image of the spectroscopic measuring field Sf is not contained in the monitor image and is displayed as a black void Bf2 (Bf1). If a preceding (t=t1) monitor image contains a partial image Df2 corresponding to the spectroscopic measuring field Sf, image processing may be carried out to paste the same onto the void Bf2.

The monitor image is temporarily stored in a storage device (memory) of an image processing unit (not illustrated). A pixel range corresponding to the slit 23 is identifiable in the monitor image, and therefore, the black image element Bf2 (t=t2, t1<t2) can be replaced with the image element Df2 (t=t1) corresponding to the slit, to constitute a monitor image Dm2' having no void.

As a result, it is possible to display, as illustrated in FIG. 3(c), the image Dm2' supplemented with the element Df2 corresponding to the spectroscopic measuring field Sf and having no void. In addition, a frame If2 is displayed to clarify the position of the spectroscopic measuring field Sf. This makes it possible, as illustrated in FIG. 3, to confirm a specific region E such as an affected part in real time in the two-dimensional monitor image and visually observe a positional relationship with respect to the spectroscopic measuring field.

The preceding monitor image is an image that has been taken just before the present monitor image and contains the partial image Df2. The preceding monitor image may be formed by combining a plurality of preceding images that contain the partial image Df2.

<Modification>

Figure 4:
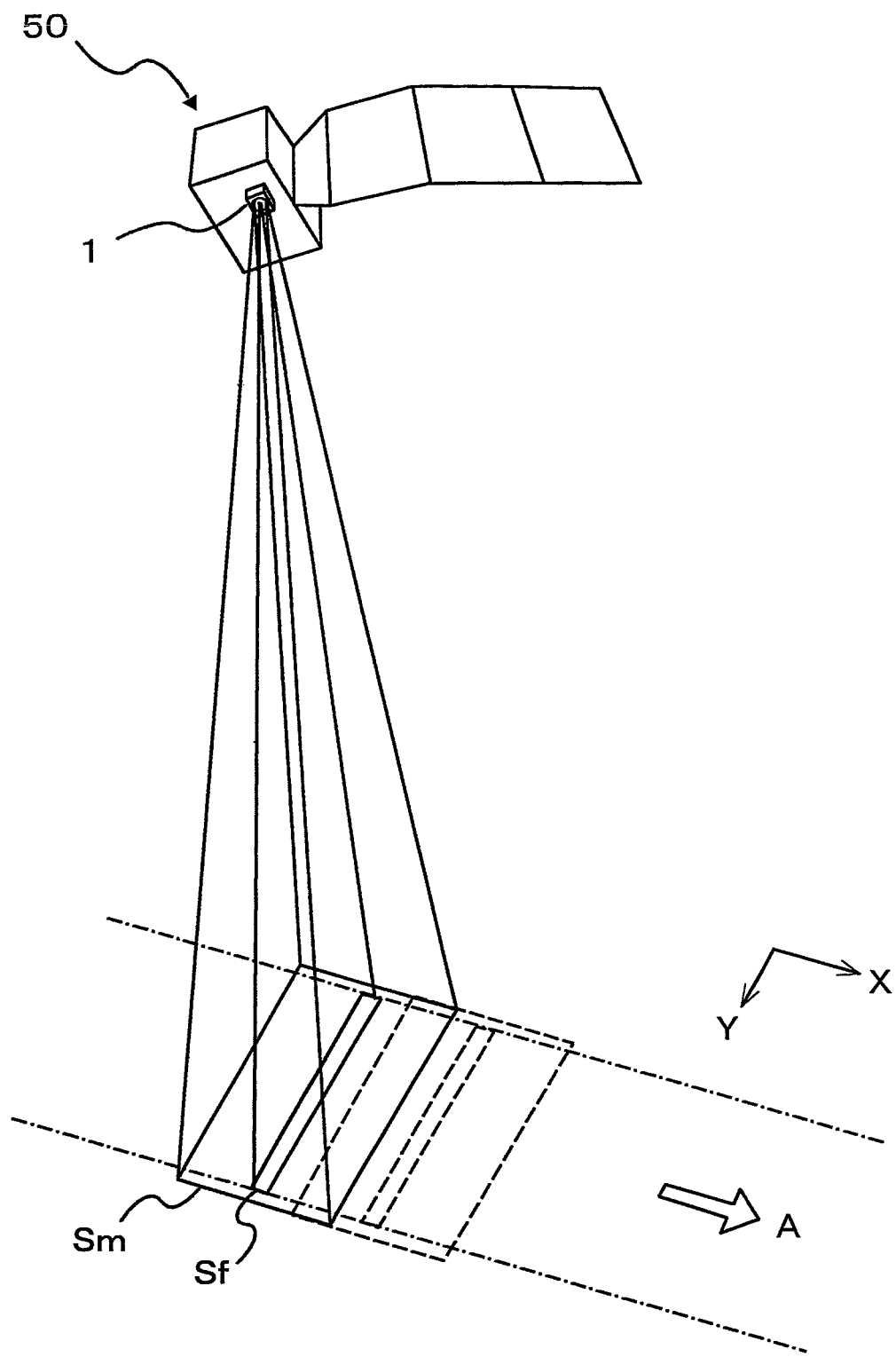
FIG. 4 is an example of the spectroscopic measuring system according to the present invention installed in an orbiting satellite.

The spectroscopic measuring system capable of monitoring a measuring object is installable in a flying object, to conduct remote sensing. FIG. 4 illustrates an example that installs the spectroscopic measuring system 1 in an orbiting satellite 50 that orbits a celestial body such as a planet. The spectroscopic measuring field Sf corresponds to an instantaneous field of view (IFOV) on the surface of a measuring object viewed through the slit 23. The peripheral measuring field Sm corresponds to an instantaneous field of view of the two-dimensional image sensor (such as CCD) installed in the two-dimensional photographing unit 40 for obtaining monitor images.

In this case, the autofocus control and scanning mechanism of the optical system (telescope) 30 are not needed. The main axis direction (Y-axis direction) of the slit is set to be orthogonal to a flying direction (scanning direction) A of the orbiting satellite 50. The spectroscopic measuring system 1 according to the present invention is compact because the partial transmission mechanism 21 having the slit mirror is integrated with the spectroscope main body 25. In addition, it adopts the slit-mirror block 21 to correctly and stably carry out spectroscopic measurement. Accordingly, it is installable in the flying object that must be lightweight and highly reliable.

The two-dimensional photographing unit 40 is able to conduct real-time monitoring. It may be provided with an image storage unit having a predetermined capacity, to temporarily store spectroscopic measurement images and monitor images that are related to each other. It is possible to store a series of image data during spectroscopic measurement, and after the measurement, transmit predetermined image data to a ground station. In a series of measurement data received on the ground, the black void image element BF2 is replaced with the image element Df2 corresponding to the slit 23, to provide the monitor image Dm2' having no void.

Effects Of Invention

As mentioned above, the present invention integrates the slit-mirror block and spectroscope main body into the spectroscopic unit, to reduce the size and weight of the apparatus. The reflection area and slit are integrated into the block, to eliminate an influence of multiple reflection at the slit and improve the strength and reliability of the apparatus.

Through the slit-mirror block, a monitor image is obtained, and therefore, the position of a spectroscopic measuring field is confirmable in real time. A preceding monitor image is used to supplement a present image of the spectroscopic measuring field, and therefore, it is easy to visually observe the position and image of the spectroscopic measuring field in real time.

(United States Designation)

In connection with United States designation, this international patent application claims the benefit of priority under 35 U.S.C. 119(a) to Japanese Patent Application No. 2010-243381 filed on Oct. 29, 2010 whose disclosed contents are cited herein.

The invention claimed is:

1. A spectroscopic measuring apparatus with monitoring capability, comprising:
    a spectroscope main body;
    an optical system, a first optical path and a second optical path passing through the optical system, the first optical path guiding a first beam from a measuring object to the spectroscope main body, the second optical path guiding a second beam from the measuring object to a two-dimensional photographing unit; and
    a reflection block transmitting the first beam passed through the optical system and reflecting the second beam passed through the optical system,
    the reflection block including:
    a reflection area reflecting beams other than the first beam; and
    a slit formed in the reflection area and positioned in the first optical path and in a focal plane of the optical system,
    wherein the spectroscope main body is arranged adjacent to the reflection block, and is integrated with the reflection block,
    the spectroscopic measuring apparatus further comprising:
    a storage configured to relate spectroscopic measurement data of the spectroscope main body and two-dimensional monitor image data of the measuring object with each other and to temporarily store the spectroscopic measurement data and the two-dimensional monitor image data, and
    an image processor configured to combine current two-dimensional monitor image data corresponding to an area within the slit together with preceding two-dimensional monitor image data of the measuring object, while the apparatus scans the measuring object.

2. The spectroscopic measuring apparatus with monitoring capability according to claim 1, wherein
    the reflection block other than the reflection area has an uniform refractive index.

3. The spectroscopic measuring apparatus with monitoring capability according to claim 1, wherein
    the optical system includes an objective optical system that is movable in an optical-axis direction and is autofocus-controlled with respect to the measuring object.

4. The spectroscopic measuring apparatus with monitoring capability according to claim 1, wherein the reflection block includes two triangle prisms bonded together with a mirror face interposed between the two triangle prisms.

5. The spectroscopic measuring apparatus with monitoring capability according to claim 1, wherein the spectroscope main body and the reflection block are integrated into a single spectroscopic unit.

6. The spectroscopic measuring apparatus with monitoring capability according to claim 1 wherein the image processor detects a supplemental image in the preceding two-dimensional monitor image data stored in the storage, which corresponds to the area within the slit in the current two-dimensional monitor image data, and
    the image processor replaces an image corresponding to the area within the slit in the current two-dimensional monitor image data with the detected supplemental image in the preceding two-dimensional monitor image data stored in the storage.

7. A spectroscopic measuring apparatus with monitoring capability, installed in a flying object that flies and travels with respect to the measuring object, the spectroscopic measuring apparatus having a first optical path that guides a first beam from a measuring object to a spectroscope main body and a second optical path that guiding a second beam from the measuring object to a two-dimensional photographing unit, the spectroscopic measuring apparatus comprising:
    an optical system, the first and second optical paths passing through the optical system;
    a reflection block transmitting the first beam passed through the optical system and reflecting the second beam passed through the optical system,
    the reflection block including:
    a reflection area reflecting beams other than the first beam; and
    a slit formed in the reflection area and positioned in the first optical path and in a focal plane of the optical system,
    a storage configured to relate spectroscopic measurement data of the spectroscope main body and two-dimensional monitor image data of the measuring object with each other and to temporarily store the spectroscopic measurement data and the two-dimensional monitor image data; and
    an image processor configured to combine current two-dimensional monitor image data corresponding to an area within the slit together with preceding two-dimensional monitor image data of the measuring object, while the apparatus scans the measuring object, wherein the spectroscope main body is arranged adjacent to the reflection block, and the spectroscopic measuring apparatus scans the measuring object in a flying direction and spectroscopically measures the measuring object.

* * * * *